United States Patent [19]

Schnabl et al.

[11] 4,438,399

[45] Mar. 20, 1984

[54] EDDY CURRENT TESTING DEVICE FOR METAL TUBES OR PIPES HAVING A QUICK RELEASE COUPLING WITH A BAYONET LOCK

[75] Inventors: Karl Schnabl; Eberhard Höppner, both of Erlangen; Hans Kastl, Neustadt, all of Fed. Rep. of Germany

[73] Assignee: Kraftwerk Union Aktiengesellschaft, Mülheim, Fed. Rep. of Germany

[21] Appl. No.: 68,549

[22] Filed: Aug. 22, 1979

[30] Foreign Application Priority Data

Aug. 28, 1978 [DE] Fed. Rep. of Germany ....... 2837486

[51] Int. Cl.³ .................... G01N 27/72; G01N 27/82
[52] U.S. Cl. .................................................. 324/220
[58] Field of Search ................................ 324/219–221, 324/262, 149; 339/108 TP, 88 R, 90 R

[56] References Cited

U.S. PATENT DOCUMENTS

| | | | |
|---|---|---|---|
| 3,029,406 | 4/1962 | Huth | 339/90 R |
| 3,254,323 | 5/1966 | Wyse | 339/108 TP |
| 3,315,163 | 4/1967 | Lutz | 339/108 TP |
| 3,363,170 | 1/1968 | Gieske | 324/221 |
| 3,402,351 | 7/1968 | Kradel | 324/149 |
| 4,153,875 | 5/1979 | Pigeon et al. | 324/220 |

FOREIGN PATENT DOCUMENTS

| | | | |
|---|---|---|---|
| 984909 | 3/1976 | Canada | 324/220 |
| 1488833 | 10/1977 | United Kingdom | 324/220 |

*Primary Examiner*—Gerard R. Strecker
*Assistant Examiner*—Walter E. Snow
*Attorney, Agent, or Firm*—Herbert L. Lerner; Laurence A. Greenberg

[57] ABSTRACT

Probe for eddy-current testing of tubes, the probe having a conically tipped guidance head and a cylindrical coil form, includes a jacket flexible in radial direction disposed between the guidance head and the coil form, the jacket being prestressed uniformly outwardly and having a diameter greater than that of the cylindrical coil form.

5 Claims, 5 Drawing Figures

EDDY CURRENT TESTING DEVICE FOR METAL TUBES OR PIPES HAVING A QUICK RELEASE COUPLING WITH A BAYONET LOCK

The invention relates to a probe for testing eddy currents in tubes or pipes, especially in steam generators of nuclear power plants, and, more particularly, to such probes having a conically pointed guidance head and a cylindrical coil form.

In a probe known heretofore from German Patent DE-PS No. 2 263 143, the coil form and the guidance head are practically combined since they are directly adjacent one another and the largest diameter of the guidance head is as large as the diameter of the cylindrical coil form. The coil form, therefore, rests against the inside of the tube to be tested after it has slid into the tube during movement of the probe by means of a thrust hose with the aid of the guidance head.

It is an object of the invention to provide or probe for testing eddy currents in tubes or pipes, the operation of which is improved over the operation of heretofore known probes of this general type. More specifically, it is an object of the invention to provide such a probe having an increased measuring accuracy and, simultaneously, an increased mobility within the tube that is being tested.

With the foregoing and other objects in view, there is provided, in accordance with the invention, a probe for testing eddy current in tubes, the probe having a conically tipped guidance head and a cylindrical coil form, comprising a jacket flexible in radial direction disposed between the guidance head and the coil form, the jacket being prestressed uniformly outwardly and having a diameter greater than that of the cylindrical coil form.

With the flexible jacket, the probe can resiliently adapt itself, with respect to the diameter, thereof, to the tube to be tested, the coil form being held at uniform spacing from the inner surface of the tube being tested. Interference with the measurement results due to partial contact of the coil form with the tube being tested is thereby avoided, although the coil form, as a rigid body, must have a smaller outer diameter than the inner diameter of the tube in order to permit the introduction of the probe into the tube to be possible at all. With the centering resulting from the invention, the coil form can be made so thin that it can reliably pass points of disturbance or interference, such as deposits or the like.

In accordance with another feature of the invention, the jacket has individual fins acting as leaf springs or may be formed entirely thereof.

In accordance with a further feature of the invention, the probe includes an elastic or rubber member surrounded by the jacket and applying prestress completely or partly.

The diameter of the flexible jacket may be constant over the entire length thereof. In accordance with an added feature of the invention, however, the diameter of the flexible jacket is larger in a middle portion thereof than at the ends thereof, whereby the friction surfaces within the tube being tested are reduced when the centering is good.

In accordance with an additional feature of the invention, the flexible jacket is located forward of the coil form in direction of introduction thereof into a tube to be tested, and including another flexible jacket located rearward of the coil form in the direction of introduction. The jacket located forward of the coil form is tapered so as to serve simultaneously as a guiding head.

By locating one flexible jacket forward of the coil form and one flexible jacket rearward of the coil form, the coil form is kept centered as much as possible from both ends. Both jackets may be of symmetrical construction at least in vicinity of the coil form, and can be held, for example. in the same manner.

In accordance with yet another feature of the invention, the probe is provided with a resilient or springy construction in vicinity of the coils per se. Exact localization of defects, preferably the determination of the extent or spread of defects or faults is thereby afforded, because the gap impairing or interfering with the measurement is not only made uniform but also as small as possible.

In accordance with yet a further feature of the invention, the probe includes a hollow support member carrying the jackets, quick-release coupling means connected to the support member at a location remote from the guidance head, coils mounted on the coil form and having connecting wires extending through the hollow support member to the quick-release coupling means.

In accordance with yet an added feature of the invention, the, quick-release coupling means comprise a plug.

In accordance with yet an additional feature of the invention, there is provided a probe for eddy-current testing of tubes, the probe having a coil form mechanically and electrically couplable to a thrust hose for moving the probe through the tubes to be tested and comprising a jacket flexible in radial direction disposed adjacent the coil form, the jacket having a side thereof facing away from the coil form, a plug forming part of a quick-release coupling with a bayonet lock located at the side of the jacket facing away from the coil form and forming a connection for the probe to the thrust hose.

In accordance with an added feature of the invention, the probe includes a tubular support member carrying the coil form and the jacket, and a hose formed of synthetic material connecting the tubular support member to the plug of the quick-release coupling.

In accordance with a concomitant feature of the invention, the probe includes a connecting member press-fitted on the plug for connecting the plug to the hose.

Other features which are considered as characteristic for the invention are set forth in the appended claims.

Although the invention is illustrated and described herein as embodied in a probe for testing eddy currents in tubes or pipes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1:
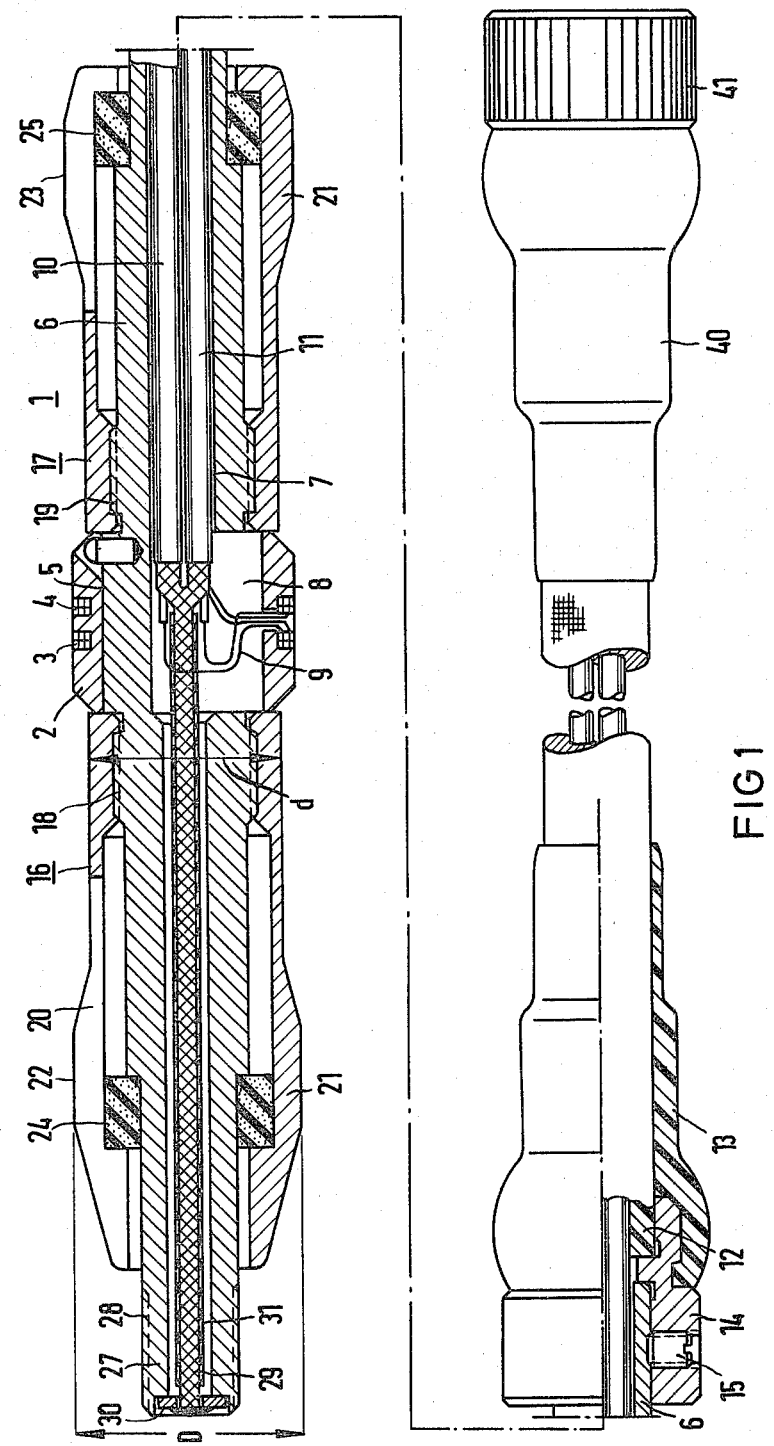
FIG. 1 is an enlarged partly longitudinal sectional view, partly broken away, of an embodiment of the eddy current probe according to the invention, suited for testing tubes in steam generators of a pressurized water reactor.

Referring now to the drawing and first, particularly, to FIG. 1 thereof, there is shown an eddy-current probe 1 constructed almost fully axially symmetrically. The most important part thereof is a cylindrical coil form 2 of polyoxymethylene wherein two coils 3 and 4 for eddy-current testing are accommodated in two parallel planes which are perpendicular to the longitudinal axis of the cylindrical coil from 2. The coil form 2 is mounted on the annular surface 5 of a support member 6, which is likewise formed of polyoxymethylene and has a central cavity 7. In vicinity of the coil form 2, the support member 6 is recessed laterally at a location thereof from the central cavity 7 up to the annular surface 5. Connecting wires 9 lead to the coil 3 and 4 through the thus-formed recess 8.

Figure 5:
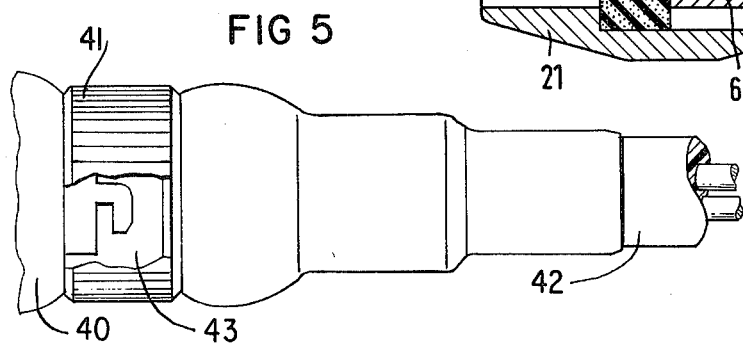
FIG. 5 is a longitudinal view, partly broken away, of the connection between the probe and a thrust hose.

The connecting wires 9 belong to two coaxial cables 10 and 11 which are set into a polyethylene tube 12 beyond the free end of the probe 1. The tube 2 is held by a molded member 13 formed of thermoplastic material and shrunk onto an adapter or connecting member 14 also formed of polyoxymethylene. The adapter 14 is fastened by a headless screw 15 to the support member 6. A plug 41 is fastened by means of an adapter 40 similar to the adapter 14 to the end of the tube 12 facing away from the free end of the probe 1. As part of a fast-acting coupler, the plug 41 affords an easily assemblable mechanical and electrical connection, such as a bayonet lock 43 to a thrust or slide hose 42, as shown in FIG. 5.

The tubular support member 6 has a smaller diameter than the coil form 2. On both sides of the coil form 2, the support member 6 carries two tubular sections 16 and 17 formed of polyoxymethylene, which are screwed onto threads 18 and 19 formed on support member 6 in vicinity of the coil form 2. The tube sections 16 and 17 are provided with slots 20 over about half the length thereof in a region thereof facing away from the thread 18 and 19, and thus form an elastic jacket with fins 21. In the illustrated embodiment, eight fins 21 are distributed over the periphery of the eddy-current probe 1.

The tube sections 16 and 17 are beefed-up or thickened in the slotted region 22 and 23 thereof. The difference in length between the largest diameter D at the respective beefed-up regions 22 and 23 of the tube sections 16 and 17, which is larger than the diameter of the coil form 2, and the smaller diameter d in the vicinity of the threads 18 and 19 is about two mm and, therefore, about 10% of the largest diameter D. In the beefed-up or enlarged region 22 and 23, a ring 24 and 25, respectively, formed of elastic material, preferably foam or sponge rubber, is disposed between the support member 6 and the respective tube sections 16 and 17. The elastic ring 24, 25 applies an uniformly outwardly acting prestressing force to the fins 21 which produces uniform contact thereof against the inner surface of the non-illustrated tube to be tested. In this manner, the coil form 2 with the coils 3 and 4 disposed thereon is held at a uniform distance from the wall of the non-illustrated tube which is to be tested.

In the embodiment shown in FIG. 1, the support member 6 has a tip 27 thereof which is provided with an outer thread 28 and protrudes from the region of the fins 21. Shielding 29 for the cables 10 and 11 is constructed in the form of a wire screen and fastened by a disk or washer 30, to which the shielding is soldered or brazed. An insulating tube 31 is slid over the shielding 29 to provide mechanical protection thereof.

Figure 2:
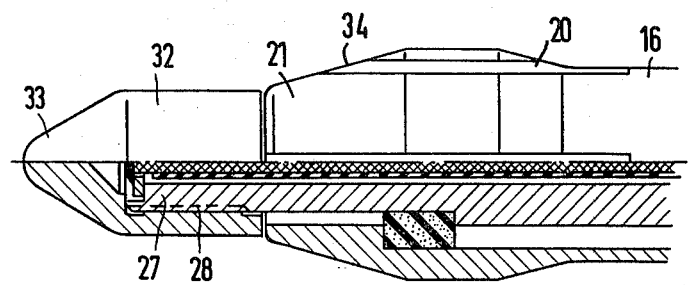
FIGS. 2, 3 and 4 are fragmentary views of FIG. 1 showing different embodiments of the tip of the probe which are advantageous for adapting the probe to special spatial conditions

In the embodiment of the invention shown in FIG. 2, a cap 32 of polyoxymethylene is screwed onto the outer thread 28 formed on the probe tip 27. The cap 32 has a smaller diameter than that of the tube sections 16 and 17, and terminates in a tip 33 of its own. Thus, a further means for centering and thereby facilitating the introduction of the probe 1 into a tube is provided in addition to an outer bevel 34 provided on the jacket 16, which acts as guidance head.

Figure 3:
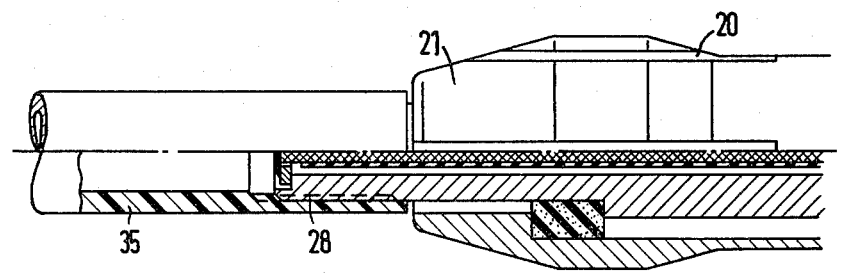

In the embodiment shown in FIG. 3, a draw or pull hose 35 formed of polyethylene is screwed onto the thread 28 formed on the probe tip 27. The pull hose 35 can be slid into the non-illustrated tube being tested, from a side opposite that at which the probe 1 is introduced into the tube being tested, so that, for introducing the probe 1, a larger force can be applied than if the probe had to be transported through the tube with the pull or thrust hose 42 from one side only.

Figure 4:
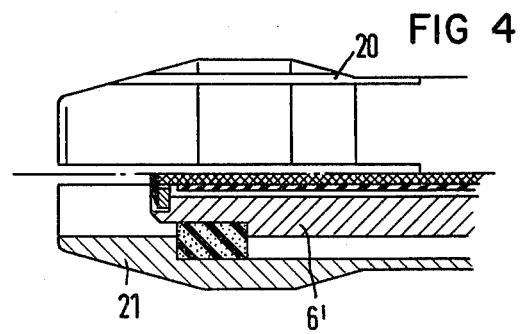

In the embodiment of the invention illustrated in FIG. 4, the support element 6' is shortened and does not protrude from but rather terminates within the fins 21.

There are claimed:

1. Probe for eddy-current testing of tubes, the probe having a coil form mechanically and electrically couplable to a thrust hose for moving the probe through the tubes to be tested, comprising an elongated support member having a central cavity containing electrically conductive cables therein, a tubular jacket flexible in radial direction and formed with a plurality of substantially axially extending leaf-springlike fins, said jackets and said fins surrounding said support member and having an end thereof disposed adjacent the coil form and another end thereof facing away from the coil form, a plug forming part of a quick-release coupling with a bayonet lock being located at said other end of said jacket facing away from the coil form and forming a connection for the probe to the thrust hose.

2. Probe according to claim 1 including a tubular support member carrying the coil form and said jacket, and a hose member formed of synthetic material connecting said tubular support member to said plug of said quick-release coupling.

3. Probe according to claim 1 including a connecting member press-fitted on said plug for connecting said plug to said hose member.

4. Probe according to claim 2 including an elastic member located at an end of said fins facing toward said plug, said elastic member being disposed between and enclosed by said jacket and said tubular support member together.

5. Probe according to claim 4 wherein said coil form has a side thereof facing away from said plug and including another jacket also formed with fins and having an end adjacent said last-mentioned side of said coil form, and another elastic member enclosed by said last-mentioned fins, together with said tubular support member.

* * * * *